(12) United States Patent
Benosman et al.

(10) Patent No.: US 10,154,235 B2
(45) Date of Patent: Dec. 11, 2018

(54) DEVICE FOR DISPLAYING AN IMAGE SEQUENCE AND SYSTEM FOR DISPLAYING A SCENE

(71) Applicants: UNIVERSITE PIERRE ET MARIE CURIE (PARIS 6), Paris (FR); CENTRE NATIONAL DE LA RECHERCHE SCIENTIFIQUE—CNRS, Paris (FR)

(72) Inventors: Ryad Benosman, Pantin (FR); Guillaume Chenegros, Trappes (FR); Serge Picaud, Avon (FR); Siohoi Ieng, Montreuil (FR); Jose-Alain Sahel, Paris (FR)

(73) Assignees: UNIVERSITE PIERRE ET MARIE CURIE (PARIS 6), Paris (FR); CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 0 days.

(21) Appl. No.: 15/128,996

(22) PCT Filed: Mar. 12, 2015

(86) PCT No.: PCT/FR2015/050615
§ 371 (c)(1),
(2) Date: Sep. 26, 2016

(87) PCT Pub. No.: WO2015/145017
PCT Pub. Date: Oct. 1, 2015

(65) Prior Publication Data
US 2017/0111619 A1  Apr. 20, 2017

(30) Foreign Application Priority Data
Mar. 26, 2014 (FR) ...................... 14 52558

(51) Int. Cl.
*H04N 9/31* (2006.01)
*H04N 5/64* (2006.01)
(Continued)

(52) U.S. Cl.
CPC ........... *H04N 9/312* (2013.01); *A61B 5/6821* (2013.01); *A61N 1/0543* (2013.01);
(Continued)

(58) Field of Classification Search
CPC ............ H04N 9/31; H04N 9/312; H04N 5/64; A61N 1/0543; A61N 1/36046; A61N 1/05;
(Continued)

(56) References Cited

U.S. PATENT DOCUMENTS

| 6,400,989 B1 * | 6/2002 | Eckmiller | A61N 1/36046 607/54 |
| 7,245,273 B2 * | 7/2007 | Eberl | G02B 27/017 345/7 |

(Continued)

FOREIGN PATENT DOCUMENTS

FR  2 975 251 A1  11/2012

OTHER PUBLICATIONS

Christoph Posch et al, "A QVGA 143 dB Dynamic Range Frame-Free PWM Image Sensor With Lossless Pixel-Level Video Compression and Time-Domain CDS", IEEE Journal of Solid-State Circuits, Jan. 2011, pp. 259-275, vol. 46, No. 1.
(Continued)

*Primary Examiner* — Trang U Tran
(74) *Attorney, Agent, or Firm* — Young & Thompson

(57) ABSTRACT

A device for displaying an image sequence in the form of a pixel matrix, includes a control unit coupled to a projector. The control unit includes an input interface designed to receive asynchronous information representing, for each pixel of the matrix, events concerning the pixel, and a (Continued)

processor designed to control the activation of each pixel of the matrix at moments determined by the respective events indicated by the asynchronous information for the pixel. The projector is disposed on a support so as to illuminate the light receptors of the eye when the device is in use and is designed to project a light flux corresponding to the pixels activated by the control unit.

8 Claims, 8 Drawing Sheets

(51) Int. Cl.
| | | |
|---|---|---|
| *A61B 5/00* | (2006.01) | |
| *A61N 1/05* | (2006.01) | |
| *G02B 27/18* | (2006.01) | |
| *A61N 1/36* | (2006.01) | |
| *G02B 27/01* | (2006.01) | |
| *G02B 26/08* | (2006.01) | |
| *G02C 11/00* | (2006.01) | |

(52) U.S. Cl.
CPC ..... *A61N 1/36046* (2013.01); *G02B 26/0833* (2013.01); *G02B 27/017* (2013.01); *G02B 27/18* (2013.01); *G02C 11/10* (2013.01); *G02B 2027/014* (2013.01); *G02B 2027/0118* (2013.01); *G02B 2027/0178* (2013.01)

(58) Field of Classification Search
CPC ...... A61N 1/36; G02B 26/08; G02B 26/0833; G02C 11/10
USPC .................................................. 348/744, 62
See application file for complete search history.

(56) References Cited

U.S. PATENT DOCUMENTS

2007/0109619 A1* 5/2007 Eberl ..................... A61B 3/113
359/17

2013/0148084 A1* 6/2013 Yanai ................... G02B 27/286
353/20
2014/0009591 A1 1/2014 Ziemeck et al.
2014/0085447 A1 3/2014 Lorach et al.

OTHER PUBLICATIONS

Christoph Posch et al, "An Asynchronous Time-based Image Sensor", IEEE, 2008, pp. 2130-2133.
Henri et al.: "Paper;Artificial retina: the multichannel processing of the mammalian retina achieved with a neuromorphic asynchronous light acquisition device;Artificial retina: the multichannel processing of the mammalian retina achieved with a neuromorphic asynchronous light acquisition device", vol. 9, No. 6, Oct. 17, 2012.
Posch C: "Bio-inspired vision", Journal of Instrumentation, Institute of Physics Publishing, Bristol, GB, vol. 7, No. 1, Jan. 12, 2012 (Jan. 12, 2012), pp. C01054, XP020217109, ISSN: 1748-0221, DOI: 10.1088/1748-0221/7/01/C01054.
Christoph Posch et al: "Biomimetic frame-free HDR camera with event-driven PWM image/video sensor and full-custom address-event processor", Biomedical Circuits and Systems Conference (BIOCAS), 2010 IEEE, IEEE, Nov. 3, 2010 (Nov. 3, 2010), pp. 254-257, XP031899745, ISBN: 978-1-4244-7269-7, DOI: 10.1109/BIOCAS.2010.5709619.
Piatkowska Ewa et al: "Asynchronous Stereo Vision for Event-Driven Dynamic Stereo Sensor Using an Adaptive Cooperative Approach", 2013 IEEE International Conference on Computer Vision Workshops, IEEE, Dec. 2, 2013 (Dec. 2, 2013), pp. 45-50, XP032575709, DOI: 10.1109/ICCVW.2013.13.
P. Lichtsteiner et al.: "A 128×128 120 dB 15 ps Latency Asynchronous Temporal Contrast Vision Sensor", IEEE Journal of Solid-State Circuits, vol. 43, No. 2, Feb. 2008 (Feb. 1, 2008), pp. 566-576.
International Search Report, dated Jun. 3, 2015, from corresponding PCT application.

* cited by examiner

DEVICE FOR DISPLAYING AN IMAGE SEQUENCE AND SYSTEM FOR DISPLAYING A SCENE

BACKGROUND OF THE INVENTION

The present invention relates to devices for displaying visual information from asynchronous information.

DESCRIPTION OF THE RELATED ART

Devices having the form of spectacles enabling a user to view a scene captured by a camera on a miniature screen, fixed to the frame or arranged on a lens, have been marketed for a few years. The camera is in general fixed to the spectacle frame so as to capture a scene in the field of vision of the user, for example for augmented reality applications.

There exists moreover vision-aid devices intended for users equipped with a visual implant responding to electrical stimulations. Some of these devices are in the form of spectacles on which there are mounted a camera that produces a video stream sent to a video processing unit that encodes the stream in order to generate an electrical stimulation signal, and an external coil for transmitting the signal, by electromagnetic induction, to an internal coil connected to a retinal implant.

These existing devices cannot however be used by persons equipped with a visual implant of the photodiode type, or persons who have benefitted from optogenetic treatment. This is because the implants or optogenetic treatment methods require light stimulation signals with a much higher intensity than that of ambient light. A vision-aid implant placed under the eye, typically comprising an electrode around which one to three photodiodes are disposed, will function effectively only if these diodes receive light seven times more powerful than that of ambient light, so that the photodiodes can emit a stimulus. Likewise, current optogenetic treatments are fully effective only if the treated eye receives light signals having a specific wavelength and a light intensity ranging from two to seven times that of ambient light. The required light powers are therefore so high that the use of the display methods implemented on conventional devices, at these power levels, would cause lesions on the visual organs of the users.

SUMMARY OF THE INVENTION

There thus exists a need for devices for displaying a scene that do not have the drawbacks of the conventional methods disclosed above. In particular, a first requirement is to provide devices for displaying a scene that it is possible to use for applications in the vision-aid domain. Another need is to provide devices for displaying a scene that are compatible with use by persons equipped with a visual implant of the photodiode type and/or persons who have benefitted from optogenetic treatment.

According to a first aspect, a device for displaying a sequence of images in the form of a matrix of pixels is proposed, comprising a control unit coupled operationally to a projector, the control unit comprising an input interface configured to receive the asynchronous information representing, for each pixel in the matrix, events concerning the pixel and a processor configured to control the activation of each pixel in the matrix at instants determined by respective events indicated by the asynchronous information for said pixel. The projector of the display device proposed is arranged on a support so as to illuminate photoreceptors of the eye during use of the device, and configured to project a light flow corresponding to the pixels activated by the control unit.

The events concerning the pixel may, according to the embodiment, correspond to variations in light for the pixel, to the detection of a shape of interest, or to the detection of a primitive, and more generally to any type of asynchronous information for the pixel.

The use of asynchronous information representing events for generating commands for activating the pixels in a matrix has many advantages. These result in particular from the fact that these signals are not sampled in time according to a predefined clock frequency, such as the clock of the frames in a conventional video signal. They provide what is called and address-event representation (AER) of a scene to be displayed. An event-based signal sequence corresponds to each pixel.

The methods for acquiring or synthesising an image sequence by frames has the drawback of producing data with high redundancy, due to the fact that each frame represents a large number of pixels of an image, or even an entire image, and that all these pixels, for which the information does not change from one image to another, generate redundancies in the data representing the image sequence. This redundancy can be only partly eliminated by a compression encoding of a conventional video signal. Conversely, the asynchronous signals make it possible to obtain a very compact representation of data relating to an image sequence, because this data, representing events for one pixel (rather than for all the pixels in a matrix or a large number of them), are not redundant from one image to another.

In activating a pixel from asynchronous information, the asynchronous character of the sequence of events can be respected—to within a temporal resolution—so as to achieve an activation that is event driven.

Thus the device proposed allows the projection, to photoreceptors of the eye of the user (photoreceptors present naturally in the eye and/or photoreceptors of a visual implant), of a light flow corresponding to the pixels activated asynchronously. The asynchronous activation of the pixels makes it possible to activate simultaneously only a small number of pixels (for example a single pixel or a group of co-located pixels) and consequently to stimulate by a light flow only a local portion of the photoreceptor region. The light intensity of such a flow, aimed only at stimulating a localised region, can then be taken to levels required for the envisaged application. In particular, the small quantity of data representing a sequence of images of an asynchronous signal of the AER type makes it possible to increase the intensity of the light signals exciting the photoreceptors of a visual prosthesis or of a visual organ to which optogenetic treatment has been applied.

In one embodiment, the control unit may also be configured so as, after activation of a pixel of the matrix at a moment determined by an event indicated by asynchronous information, to repeat the command activating said pixel substantially at the same activation level at moments defined by a refresh sequence.

The activation of a pixel from asynchronous information thus makes it possible to consider the activation of a pixel only when an event corresponding to this pixel is detected in the input data representing for example a sequence of images, and to carry out refresh activations only at a much lower frequency than that of conventional display methods.

In one embodiment, the reception of the asynchronous information may comprise the reception of a signal carrying the asynchronous information, and the command activating a pixel may comprise the detection in the signal of information representing an event.

In addition, the refresh sequence may define moments of activation of the pixel separated by an interval of time. This interval of time between an event-based activation and a refresh activation, or between two refresh activations, may for example be determined according to the retinal persistence of the human eye. The retinal persistence of the human eye constitutes a limit threshold that it is preferable not to exceed for effecting a refresh display of the pixel, at the risk of damaging the visual comfort of the user. For example, this interval of time will be chosen between 40 ms and 800 ms, and preferably between 40 ms and 150 ms, in order to avoid scintillation effects, knowing that a longer interval of time corresponds to a lower refresh frequency and a reduction in the flow of display commands and associated calculations.

According to one embodiment of the device, the projector comprises a matrix of micromirrors, a unit controlling the matrix of micromirrors, a control input for receiving the pixel activation commands, and an optical input for receiving a light flow.

According to one embodiment of the device, the projector support is in the form of a pair of spectacles, the projector being placed on a surface of the spectacles.

According to another aspect, a system is proposed for displaying a scene, comprising a display sub-system coupled operationally to an acquisition sub-system, in which the display sub-system comprises a device according to the first aspect, and in which the acquisition sub-system comprises a sensor disposed facing the scene, coupled operationally to a processing unit configured to generate asynchronous information representing events for each pixel.

According to one embodiment of the system, the sensor is a light sensor comprising an optic for acquiring the scene and a matrix of photosensitive elements.

According to one embodiment of the system, the sensor is mounted on the projector support so that the scene captured corresponds substantially to the visual scene of a user of the device.

According to one embodiment of the system, the projector support is in the form of a pair of spectacles, the projector is mounted on a first surface of the spectacles, the sensor is mounted on the top part of the spectacles mount, and the control unit of the device and the processing unit of the acquisition sub-system are mounted on a second surface of the spectacles.

In a variant, a system can be provided in which the projector support is in the form of a pair of spectacles, the projector is mounted on a first surface of the spectacles, and the sensor, the control unit of the device and the processing unit of the acquisition sub-system are mounted on a second surface of the spectacles.

BRIEF DESCRIPTION OF THE DRAWING FIGURES

Other particularities and advantages of the present invention will emerge from the following description of non-limitative example embodiments with reference to the accompanying drawings, in which.

Figure 4A:
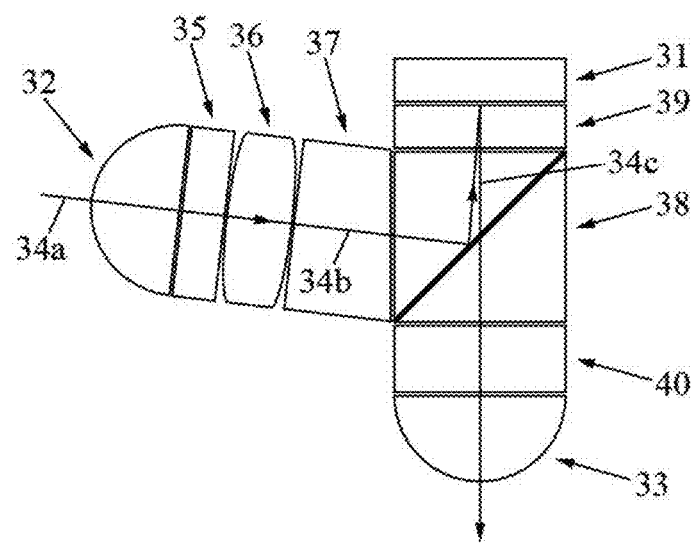
Figure 4B:
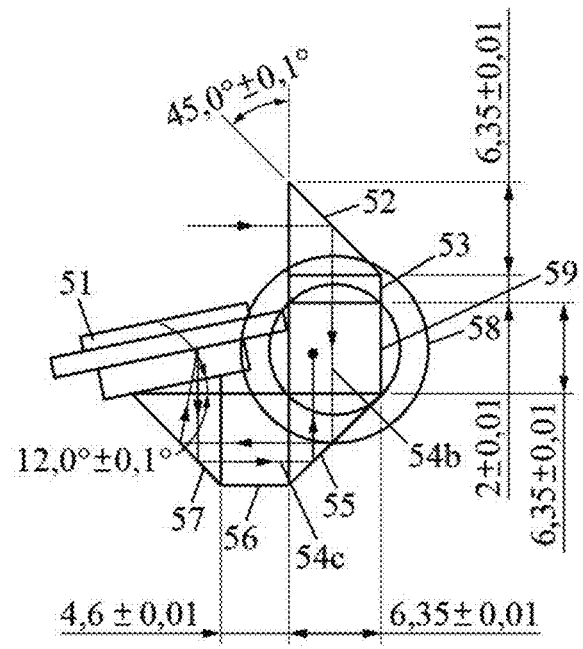
Figure 4C:
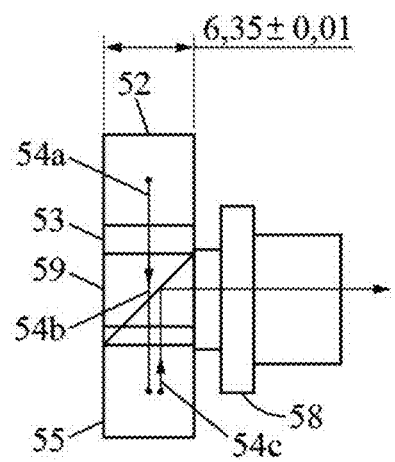
Figure 6A:
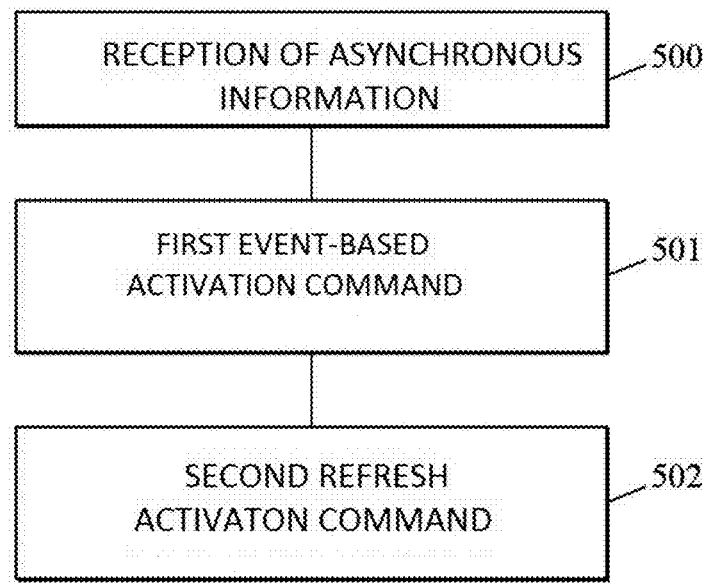
Figure 6B:
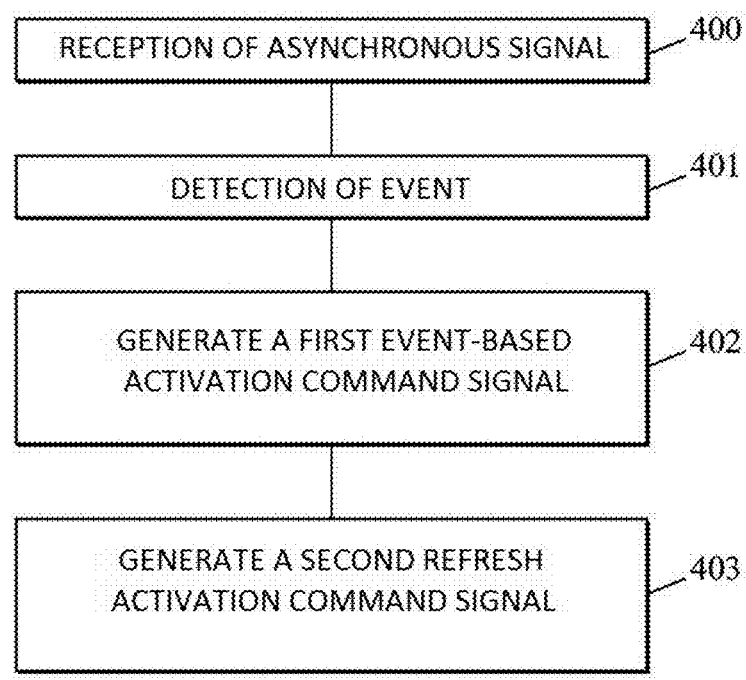
Figure 7A:
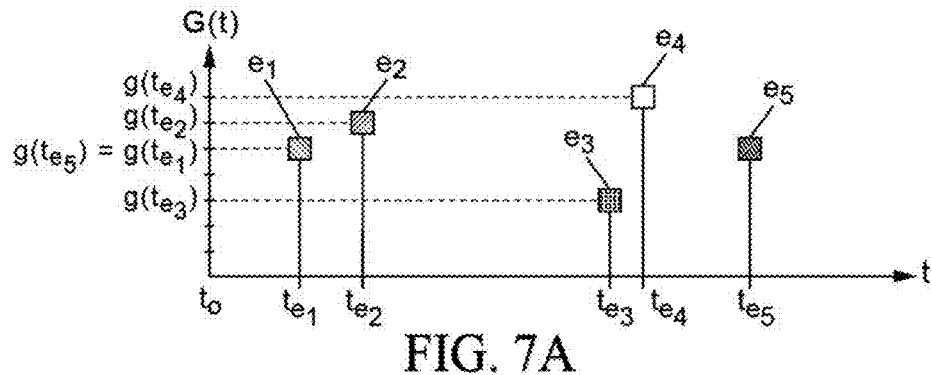
Figure 7B:
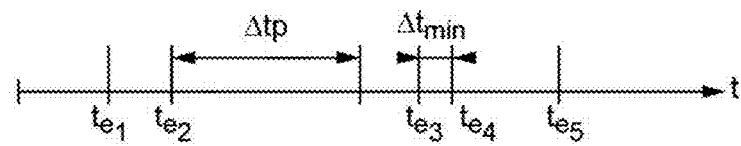
Figure 7C:
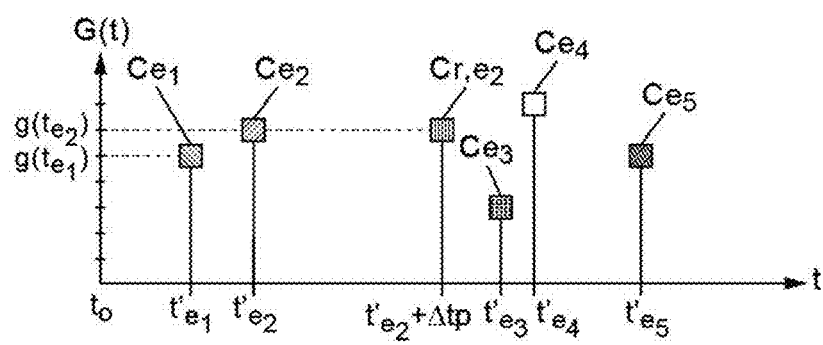
Figure 7D:
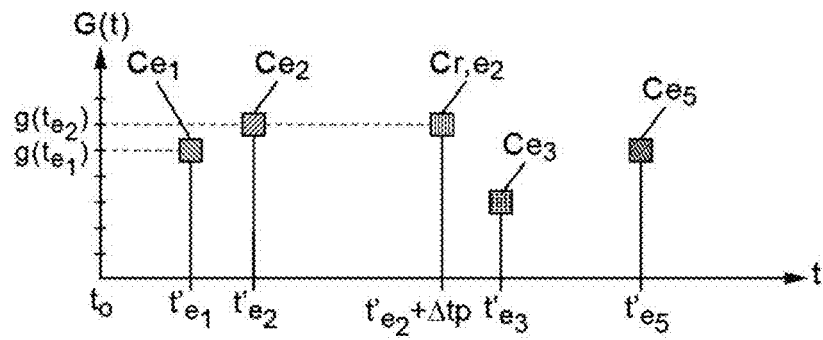
Figure 8:
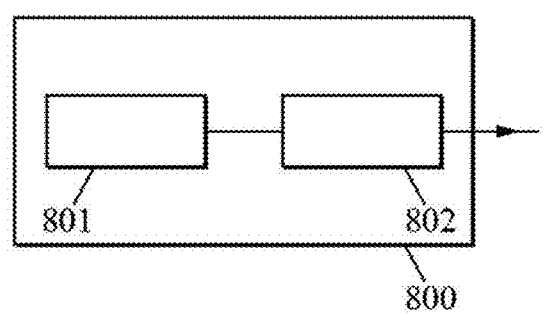
Figure 9A:
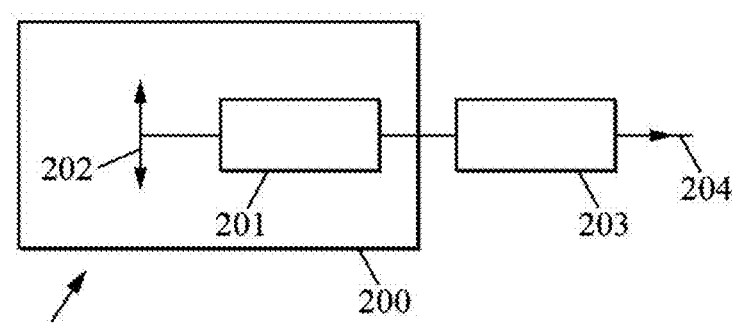
Figure 9B:
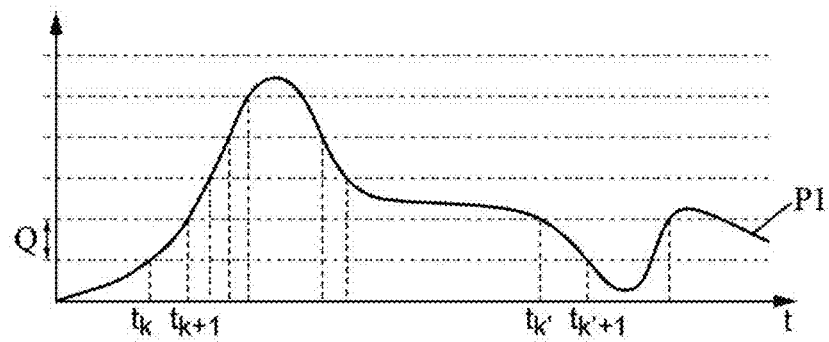
Figure 9C:
Figure 9D:
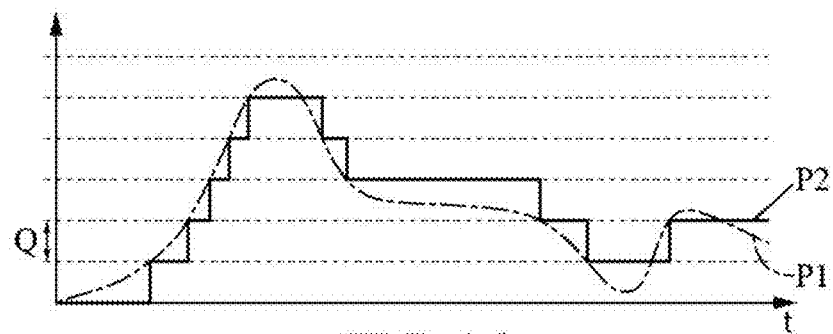

FIGS. 4a, 4b, and 4c are block diagrams of an optical sub-system of a projection device according to particular embodiments of the device proposed;

FIGS. 5a, 5b, 5c, 5d illustrate pairs of spectacles on which a device for displaying an image sequence and a light sensor according to embodiments of the device and of the system proposed are mounted;

FIGS. 6a and 6b are diagrams illustrating pixel activation control methods used by the device and system proposed in one embodiment;

FIGS. 7a and 7b are diagrams showing a time sequence of events received in an asynchronous signal for implementing the device and system proposed;

FIGS. 7c and 7d are diagrams showing a time sequence of pixel activation commands generated according to particular embodiments of the device and system proposed;

FIG. 8 is a block diagram of a system for displaying a scene according to one embodiment of the system proposed;

FIG. 9a is a block diagram of a light-acquisition device able to generate an asynchronous signal according to one embodiment of the system proposed;

FIG. 9b is a diagram showing an example of a light-intensity profile at a pixel of an asynchronous sensor;

FIG. 9c shows an example of the signal delivered by the asynchronous sensor in response to the intensity profile in FIG. 9b;

FIG. 9d illustrates the reconstruction of the intensity profile from the signal in FIG. 9c.

DETAILED DESCRIPTION OF THE INVENTION

In the following detailed description of embodiments of the invention, many specific details are presented in order to give a more complete understanding. Nevertheless, a person skilled in the art may realise that embodiments may be put into practice without these specific details. In other cases, well-known features are not described in detail in order to avoid unnecessarily complicating the description.

The invention will be described in the non-limitative context of asynchronous information representing, for a pixel in a matrix of pixels, events corresponding to variations in light for the pixel. The devices and systems proposed are however not limited to this particular embodiment, the events concerning the pixel being able, according to the embodiment, to correspond to variations in light for the pixel, to the detection of a shape of interest or to the detection of a primitive, and more generally to any type of asynchronous information for the pixel.

Figure 1:
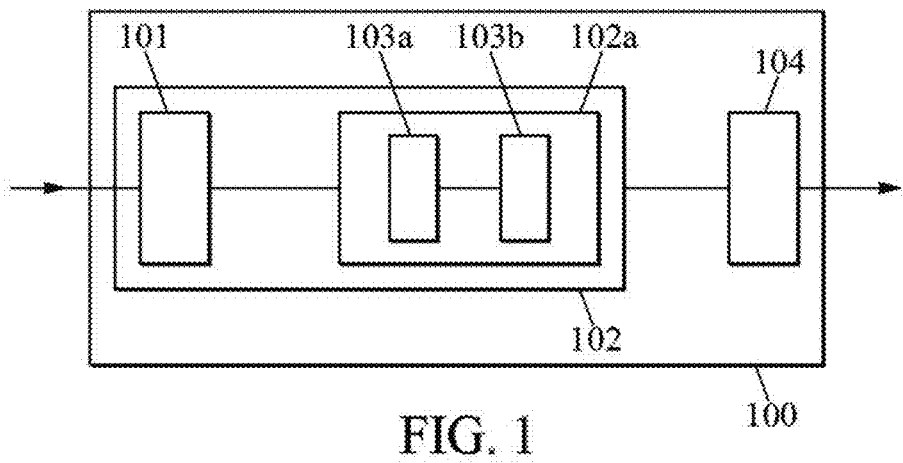
FIG. 1 is a block diagram of a device for displaying a sequence of images according to one embodiment of the device proposed.

FIG. 1 shows a device 100 for displaying a sequence of images comprising a control unit 102 for controlling the activation of pixels, and a projector 104 for projecting a light flow onto the eye of a user.

Hereinafter, the images to be displayed are considered in the form of a matrix of elementary objects referred to as pixels.

In one embodiment of the device proposed, the control unit 102 comprises an input interface 101 for receiving asynchronous information. The asynchronous information received on the input interface (101) represents, for each pixel in the matrix, events corresponding to variations in light for the pixel. It thus corresponds to a sequence of images, each considered in the form of a matrix of pixels.

The input interface 101 may be configured to receive the asynchronous information in various forms, or formats, corresponding to various embodiments of the device. It may also be provided according to various standard formats, such as, for example, the USB (universal serial bus) format. The device proposed is not limited to a particular format of asynchronous information, or carrier of this information (for example an asynchronous signal carrying information representing a flow of events), or a specific input interface format.

The asynchronous information may in fact be generated by various means. For example, it may be carried by an asynchronous signal produced by an asynchronous vision sensor and received on the input interface (101). It may also result from the encoding of a sequence of synthesis images producing a set of data received on the interface (101).

In general terms, the asynchronous information represents events relating to the pixels in the matrix. In a particular embodiment, the asynchronous information indicates, or signals, events relating to one of more pixels. It may for example comprise data that identify events with their respective characteristics.

According to one embodiment, the asynchronous information for a pixel may be carried by a succession of impulses or lines, positive or negative, positioned in time and at instants $t_k$ depending on the light profile for the pixel. These lines may be represented mathematically by positive or negative Dirac peaks and each characterised by an emission instant $t_k$ and a sign bit. The information corresponding to an event for a pixel may comprise a first item of information relating to an instant at which the event occurs, and a second item of information relating to a light characteristic for the pixel at this instant.

The form of the asynchronous information for a pixel may be different from a succession of Dirac peaks, the events represented being able to have any temporal width or amplitude or waveform.

The input interface 101 thus receives, in this embodiment, for each pixel of position p=(x; y), data representing a series of binary pulses, which can be modeled by ON or OFF events generated asynchronously at instants $t_k$.

The information corresponding to an event comprises position information for the pixel for which the event occurred (for example the pair (x; y) of the row and column numbers in the matrix of pixels), information on the time at which the event occurred (for example a discrete time value with respect to a reference), and event-type information (for example a bit for coding events of two types).

In a particular embodiment, the input interface 101 may be configured to receive an asynchronous signal carrying information representing a flow of events, each defined by a quadruplet e(x; y; t; ON/OFF) giving the position p=(x; y) of the pixel with which the event is associated, the instant t at which the event was detected, and the type (ON or OFF) of the event.

In another particular embodiment, the asynchronous signal received at the input of the interface 101 carries information representing a flow of events where each event is defined by a quadruplet e(x; y; t; g) giving the position p=(x; y) of the pixel with which the event is associated, the instant t at which the event was detected, and a level of grey g associated with the event.

The control unit 102 also comprises a data processing 102a comprising a processor 103a coupled operationally to a memory 103b and to the input interface 101. According to the embodiment, the memory 103b may contain software instructions which, when they are executed by the processor 103a of the data-processing unit 102a, cause this unit 102a to effect or control the input interface parts 101, a pixel activation command according to the various methods described herein, and transmission of the commands to the projector 104. The processing 102a may be a component implementing a processor or a computing unit for generating pixel activation commands according to the various methods described and controlling input interfaces 101 and the projector 104 of the device 100.

Furthermore, the input interface 101, the data-processing unit 102a, the processor 103a and/or the memory means 103b may, separately or conjointly, be implemented in software form, as described above, in hardware form, such as an application-specific integrated circuit (ASIC), or in the form of a combination of hardware and software elements, such as for example one of more software programs intended to be loaded and executed respectively on one of more components of the FPGA (field-programmable gate array) type. They may be implemented, separately or conjointly, in the form of an electronic circuit, or in one of more electronic components (chip or chipset).

Likewise, various embodiments of the device 100 may be envisaged. For example, the input interface 101, the data-processing unit 102a and/or the memory means 103b may be implemented on an electronic asynchronous information processing module coupled operationally to an electronic projection module that implements the components of the projector 104.

The control unit 102 generates pixel activation commands, the format of which is adapted to the input interface of the projector 104.

In a particular embodiment of the device, the output interface of the control unit 102 is configured to generate an output signal with a suitable format for controlling a video projector using micromirror matrix technology (DMD, for digital micromirror device). This type of projector is sometimes referred to by the acronym DLP, for digital light processing, and functions with a light source that illuminates a matrix of micromirrors that vibrate according to the quantity of light to be reflected. The vibrations of each mirror take place about two positions corresponding respectively to inclinations about an axis, one in which the light is reflected by the mirror towards an output optic, and the other in which the light is reflected by the mirror towards an absorbent surface and is therefore not projected. Each mirror in the DMD matrix projects light for a pixel in the matrix of pixels forming the projected image.

Some DLP projectors are also capable of illuminating pixels with various levels of grey, and can therefore receive activation commands for each pixel comprising information relating to a level of grey with which the pixel is to be illuminated. It is possible for example to use a DLP projector capable of managing 1024 levels of grey, and providing it with activation commands according to the methods described in which the illumination level of grey of a pixel is coded in 10 bits.

Figure 2:
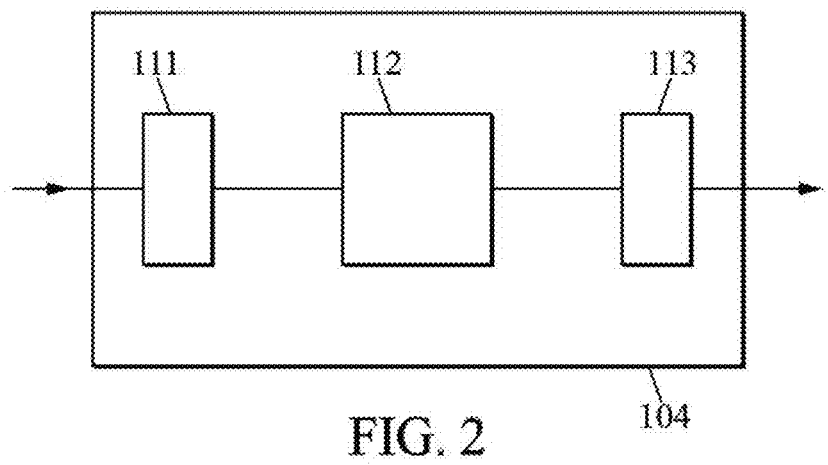
FIG. 2 is a block diagram of a projection device according to one embodiment of the device proposed.

FIG. 2 shows an example of use of the projector 104 according to a particular embodiment of the proposed device using a DLP projector.

The projector 104 comprises an input interface 111, a DMD matrix control unit 112 and an optical sub-system 113 comprising the DMD matrix.

The input interface 111 is coupled operationally to the control unit 102 of FIG. 1, and is able to receive pixel activation commands generated by the control unit 102. This coupling can be provided in accordance with various standard formats, such as for example the USB (universal serial bus) format.

The DMD matrix control unit controls the positioning of each mirror of the DMD matrix according to the pixel activation commands received by the interface 111.

The spatial resolution for control of the micromirrors may be chosen according to the application envisaged and the size of the micromirror matrix of the DMD used. For example, it is possible to keep a spatial resolution of around one pixel and illuminate one pixel without activating its neighbours, and therefore activate only one micromirror. It is also possible, in another embodiment, to group together pixels in packets, for example 3×3 pixels, in order to generate various levels of grey according to the number of pixels activated in the packet, and to activate the corresponding micromirrors.

Moreover, the input interface 111 may be configured to receive pixel activation commands in various forms, or formats, corresponding to various embodiments of the device. The proposed device is not limited to a particular pixel activation command format, or a specific input interface format. The format of the pixel activation commands will preferably be provided so as to be compatible with the input interface 111 and the control unit 112.

For example, the pixel activation commands received by the input interface 111 may, in one embodiment, relate to only one pixel in the matrix, since the input interface 111 and the control unit 112 are capable of functioning in individual pixel addressing mode.

It is however possible, in another embodiment of the device, to use a projector that functions in frame mode, taking advantage of the high values (in comparison with other types of projector) of temporal resolution of existing DLP projectors (1440 Hz, 4 kHz, 22 kHz). In this operating mode, the activation commands will comprise frames in which only the pixels that are the subject of the activation command are switched on.

The control unit 112 comprises a data processing unit comprising a processor coupled operationally to a memory (not shown in the figure). According to the embodiment, the memory may contain software instructions which, when they are executed by the processor of the data-processing unit, cause this unit to effect or control the input interface 111 and control parts of the DMD. The processing unit may be a component implementing a processor or a computing unit for generating control commands for the DMD and control of the input interface 111.

Furthermore, the input interface 111 and the various components of the control unit 112 may, separately or conjointly, be implemented in software form, as described above, in hardware form, such as an application-specific integrated circuit (ASIC) or in the form of a combination of hardware and software elements, such as for example one or more software programs intended to be loaded and executed respectively on one or more components of the FPGA (field-programmable gate array) type. They may be implemented, separately or conjointly, in the form of an electronic circuit, or within one or more electronic components (chip or chipset).

Figure 3:
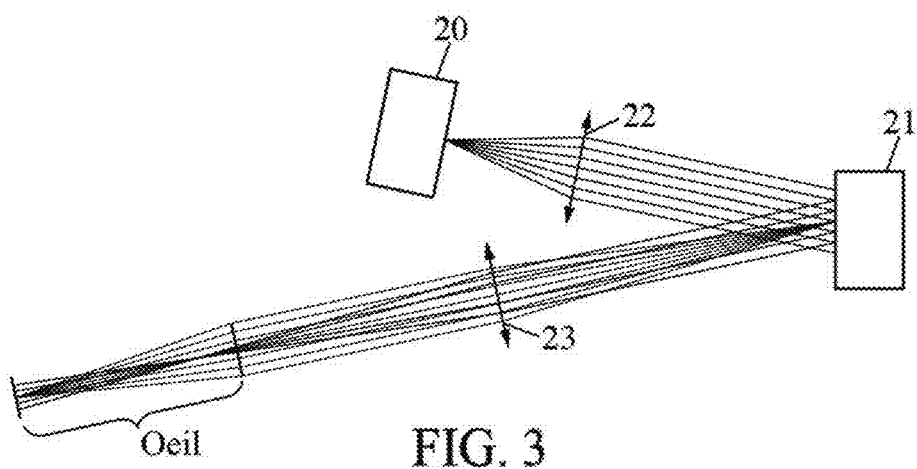
FIG. 3 is a block diagram of an optical sub-system of a projection device according to one embodiment of the device proposed.

FIG. 3 illustrates the architecture of the optical sub-system of the projector 104 according to a particular embodiment of the proposed device.

FIG. 3 shows a light source (20) arranged to emit an optical projection signal in the direction of a micromirror matrix (21). This optical projection system is adapted according to the amplification used by the device and the regulations in force. For example, in the case of the use of the device by a person equipped with a visual photodiode implant, the optical projection system will be adapted so as to provide a light intensity per pixel that stimulates the photodiodes of the implant. Likewise, in the case of the use of the device by a person who has benefitted from optogenetic treatments, the optical projection system will be adapted to provide a light intensity per pixel at wavelengths specific to this application, which stimulate the treated zone. The light source (20) is therefore chosen with in particular a spectral range and an intensity corresponding to the application envisaged. The light source (20) may for example be a laser source, or a non-coherent light source. It is preferably chosen so as to be portable, so that the user of the proposed device can easily transport the device and all the elements accompanying it (light source, electrical supply or supplies etc.).

Furthermore, the light source (20) may be offset and the optical projection system that comes from it be transported so as to illuminate the micromirror matrix, for example by means of an optical fibre (not shown in the figure). In this case, the light source (20) may comprise a laser diode coupled to an optical fibre to transport the light signal to the DMD component.

A first collimation lens (22) makes it possible to obtain an optical projection signal focused on the whole of the surface of the micromirror matrix used. This lens will therefore be arranged and positioned according to the DMD component (21) chosen and the light source (20).

The light beam issuing from the first lens (22) illuminates the matrix of micromirrors, which is positioned so that the micromirrors, positioned so as to reflect light to an output optic, reflect the light in a chosen direction so as to illuminate the area of the eye in which the photodetectors that it is sought to stimulate are situated (whether they be photodetectors present naturally, treated or not by optogenetics, or photodetectors of an implant). An arrangement of the optical sub-system that makes it possible to illuminate locally the foveal area of the eye will preferably be chosen.

In one embodiment, the matrix of micromirrors is positioned so that the micromirrors reflect the light towards an output optic in a direction substantially aligned on the optical axis of the eye.

A second collimation lens (23) collects the light reflected by a micromirror or a group of co-located micromirrors in a light beam with a cross section with dimensions corresponding to that of the area of the eye to be illuminated. Preferably, the second lens will be arranged so that the light beam that comes from it illuminates this area of the eye locally on a part corresponding to the position of the micromirror or of the group of micromirrors in the DMD matrix.

The optic of the eye functions in fact like a focusing lens, the object focal plane of which corresponds to the foveal region. The beam issuing from the second lens 23 is thus focused so as to stimulate the foveal region locally.

It is moreover possible to make provision, in a particular embodiment, to add to the second lens 23 a focusing lens to correct vision defects, such as for example a liquid lens for focusing on objects that are situated at a distance that may range from around ten centimeters to infinity. This liquid lens can be controlled for example by a potentiometer enabling the user of the device to choose from several vision modes, such as for example near vision, vision at 1.50 m and far vision.

In one embodiment, the beam issuing from the lens 23 is sized so as to illuminate a region a little wider than the foveal region. The beam for example may have a diameter of around 4.5 mm, making it possible to prevent losses of illumination of the foveal region when the eye moves.

FIG. 4a illustrates a first embodiment of the optical sub-system of the projector.

In FIG. 4a, a collimation lens 32 combined with a matrix of lenses (microlens array) 35 is found, for concentrating the light of a light beam 34a issuing from a transport optical fibre coupled with a light source (neither shown in the figure), into a projection optical signal 34b able to illuminate all the micromirrors in the matrix of micromirrors (DMD) 31 with the required characteristics (in particular power and wavelength).

The matrix of lenses makes it possible to limit the diffraction caused by the large number of micromirrors. Thus, in one embodiment of the optical sub-system of the projector using a DMD component, a matrix of lenses can be inserted on the light path, optionally combined with a modulation carried out on the optical fibre, in order to reduce the speckle effect.

An optical unit composed of a lens 36 and an optical prism 37 makes it possible to offset the direction of the projection optical signal by an angle corresponding to the pivot angle of the mirrors of the DMD along their pivot axis. For example, some DMD components function with micro-mirrors that pivot about an axis at an angle of 12°. They therefore reflect the light in a direction offset by 12° with respect to the axis perpendicular to the matrix. The emission of light towards the matrix with an angle of 12° compensates for this difference.

The projection optical signal 34b is next reflected on the dichroic mirror 38 (polarised beam splitter) in order to be directed towards the matrix of micromirrors 31. A quarter-wave plate 39 is placed between the matrix of micromirrors 31 and the dichroic mirror 38 on the path of the stimulation optical signal 34c issuing from the reflection by the matrix of micromirrors 31 in order to modify the polarisation of the signal 34c so that it can pass through the dichroic mirror 38 towards the output optic.

The output optic comprises an optical window 40 and a second collimation lens 33 fulfilling a role corresponding to that of the second collimation lens 23 in FIG. 3.

FIG. 4b illustrates a second embodiment of the optical sub-system of the projector.

The light beam 54a, for example generated by a laser diode and transported by optical fibre towards the optical sub-system of the projector, is reflected by an optical prism 52 situated at the entry to the optical sub-system. FIG. 4b shows a collimation lens 53, optionally combined with a matrix of lenses, for concentrating the light of the light beam 54a issuing from a transport optical fibre into a projection optical signal 54b able to illuminate all the micromirrors in the matrix of micromirrors (DMD) 51 with the required characteristics (in particular power and wavelength).

An optical unit composed of a dichroic mirror 59, a first optical prism 55 separated from a second optical prism 57 by a lens 56, guides the projection optical signal 54b towards the matrix of micromirrors of the DMD component 51. As before, the offset in projection introduced by the DMD component is compensated for by positioning the latter offset by a corresponding angle (in the example illustrated in the figure, the angular offset is 12°).

The path of the stimulation optical signal 54c issuing from the reflection by the matrix of micromirrors 51 is the opposite to that of the projection optical signal 54b of the matrix of the DMD component as far as the dichroic mirror 59, where the stimulation optical signal 54c is reflected towards the output optic.

The output optic comprises an optical window and collimation lens unit 58 fulfilling a role corresponding to that of the second collimation lens 23 in FIG. 3.

The element 52, 53, 55, 58 and 59 described above are also shown in FIG. 4c, where the path of the light beam 54a and of the stimulation optical signal 54c in these components can be seen, seen at a different angle from the one presented in FIG. 4b.

The dimensional information for the various components indicated in FIG. 4b illustrate an example embodiment of the optical sub-system that makes it possible to obtain equipment of very small size, and sufficiently compact to be mounted on the internal face of a spectacle lens as described below.

The associated dimensions and tolerances indicated in FIGS. 4b and 4c are expressed in mm.

Returning to FIGS. 1 and 2, the projector 104 is mounted on a support so as to direct the stimulation optical signal issuing from the optical sub-system of the projector towards the region of the eye that it is wished to illuminate.

Figure 5A:
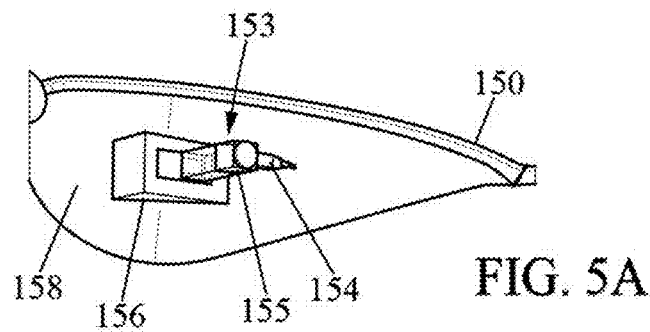
Figure 5B:
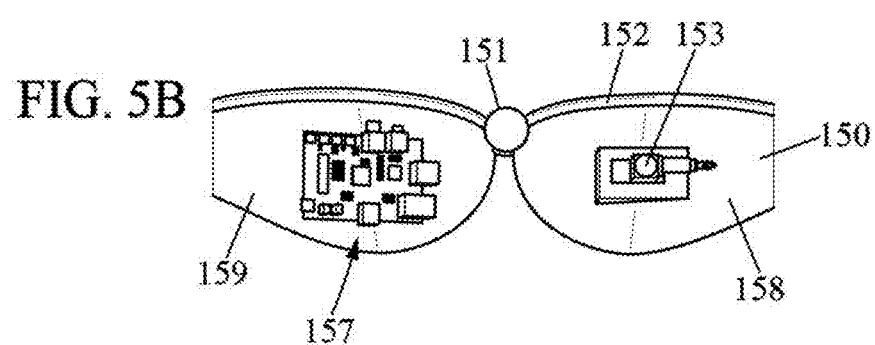
Figure 5C:
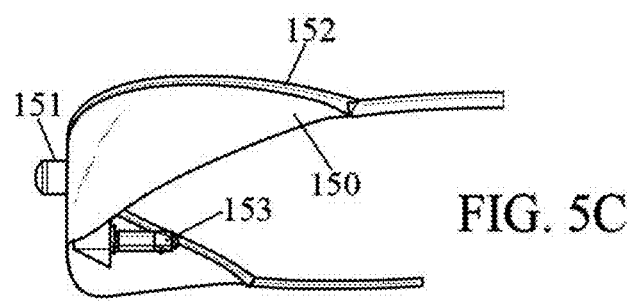

This support may be in the form of a pair of spectacles 150, as illustrated in FIGS. 5a, 5b and 5c, which show a projector module 104, 153 mounted on the internal face of a lens of a pair of spectacles.

This support may also be in the form of a mask, or of a helmet, and preferably will be conformed so as to be able to be positioned on the head of the user, and the projector arranged on the support so as to illuminate photoreceptors of the eye showing use of the device.

FIG. 5a shows a pair of spectacles 150 on which a projector module 153 is mounted. The projector module comprises an electronic sub-system and an optical sub-system that can be produced according to the example embodiments described above.

The projector 153 illustrated in FIG. 5a comprises an optical-fibre coupling interface 154, an output optic for the photoreceptor-stimulation optical signal 155, and an opto-electronic unit 156 comprising a matrix of micromirrors.

The projector module may comprise a DLP projector controlled by using the methods described below, which may for example comprise a DMD component of size 4.6 mm×5.2 mm, and support a display resolution, that is to say a size of the image displayed in pixels, of 608×684 pixels (corresponding to the WVGA standard) and a temporal resolution ranging up to 1440 Hz. These components have a sufficiently small size to enable the projector module to be mounted on a pair of spectacles as illustrated in FIGS. 5a, 5b and 5c.

Pixel-activation control methods that can be used in the proposed device are described below.

With reference to FIGS. 1 and 6a, the pixel-activation control unit 102 independently controls each pixel in a matrix of pixels for activation of this pixel. The device 100 receives (500), by means of the input interface 101, asynchronous information representing events corresponding to variations in light for the pixel.

For example, for a pixel at position $(x_o, y_o)$ in the matrix of pixels (a pixel positioned on the row of index $x_o$ and on the column of index $y_o$ in a matrix M×N, with $x \in \{0, \ldots, M-1\}$ and $y \in \{0, \ldots, N-1\}$), the information received will comprise the asynchronous information for the position pixel $(x_o, y_o)$.

The asynchronous information is processed by the data processing unit 102a in order to identify an event for the pixel so as to demand (501) a first activation of the pixel at an activation instant determined by the event identified.

The identification of an event will be able to refer to events characterised by a first item of information indicating an instant when the event occurs, and a second item of information relating to a light characteristic for the pixel at a corresponding instant. For example, the identification of an event will be able to comprise the detection of two peaks or pulses in a signal carrying the asynchronous information, the first indicating an instant when the event occurred and the second a level of grey characteristic of the event for the pixel.

In the embodiment in which the events are characterised by the instant of occurrence of any variation in light intensity beyond a threshold and the direction of this variation, the activation command may comprise a level of illumination of the pixel determined by taking account of the detected variation applied with regard to the illumination of the previous pixel activation command.

In the embodiment in which the events are characterised by the instant of occurrence of a variation in light intensity beyond a threshold and a level of grey associated with this variation, the activation command will be able to comprise a level of illumination of the pixel corresponding to the level of grey determined following the detection of the event.

This first activation of the pixel is therefore demanded on identification of an event for a pixel using the asynchronous information received at the input of the device for displaying a sequence of images 100. In a particular embodiment, the activation is controlled as soon as an event is identified for a pixel, for the processing time necessary for the system 100 for processing the information relating to the event. In a variant, the system 100 will be able to maintain an activation time reference, on the basis of which the activations of the pixels will be controlled at instants corresponding respectively to the events identified for each pixel. As described previously, each event can be characterised by an instant of occurrence and one of more values corresponding to respective items of light information (light intensity, level of grey, colour, etc.).

In a particular embodiment of the proposed device, a second activation of the pixel will be able to be demanded (502) following the first activation in order to repeat it at respective instants defined by a refresh sequence. The first activation can therefore be followed by one or more activations intended to refresh the activation demanded on identification of an event.

Provision can be made for the refresh sequence to define instants of activation of the pixel separated by an interval of time. This interval of time may be common to all the pixels in the matrix or defined for each pixel or for various subsets of pixels. It may in particular be determined according to the retinal persistence of the human eye. This makes it possible to choose refresh interval values that are sufficiently great to prevent the display of redundant information at a high frequency to the detriment of the efficacy of the system, while taking account of the duration of the retinal persistence of the previous activation. For example, the refresh time interval may be chosen between 40 ms and 150 ms, knowing that the higher the value chosen, the more the pixel activation control will gain in efficacy by preventing redundant activations accordingly.

A second activation of the pixel can therefore be demanded in order to effect a refreshing of the activation of the pixel during the interval of time thus determined and running as from the activation of the pixel following the previous activation command.

This previous activation command may be an activation command on event identification as described above, or a refresh activation command in the case for example where no event-based identification activation has been demanded for a period of time corresponding to the refresh time interval running from the previous activation of the pixel.

FIG. 6b illustrates a particular embodiment of the method proposed, in which the device 100 of FIG. 1 receives a signal carrying asynchronous information, processes this signal in order to detect events, and then generates pixel activation commands transmitted to the projector 104 using a format appropriate to the latter.

With reference to FIGS. 1 and 6b, the device 100 for displaying a sequence of images receives (400), by means of the input interface 101, an asynchronous signal carrying information representing events corresponding to variations in light for the pixel. The asynchronous signal is processed by the data processing unit 102a in order to detect (401) information representing an event for the pixel.

As described above, according to the embodiment of the proposed device, the detection of information representing an event can relate to events characterised by the instant at which a variation occurred in light intensity beyond a threshold (which may, in one embodiment, be specific to the pixel) and the direction of this variation, or relate to events characterised by the instant at which a variation occurred in light intensity beyond a threshold (which may, in one embodiment, be specific to the pixel) and a level of grey associated with this variation.

The information representing an event for the pixel is processed by the data processing unit 102a in order to generate (402) a first pixel activation command signal. The shorter the time for generating and transmitting a pixel activation command as from the moment when an event is detected by the pixel, the better will the asynchronous character of the input signal of the device 100 for displaying a sequence of images be respected. A real-time processing will thus be preferred in order to obtain an almost instantaneous activation according to the events detected for each pixel.

The first activation command, generated on detection of an event for a pixel, is transmitted to the projector 104 with which the control unit 102 is interfaced.

As described above, this first pixel activation, carried out on detection of an event for the pixel, can be followed by a second activation intended to refresh the previous event-detection-based activation. In this case, the second activation gives rise to the generation (403) of a second activation command. This second activation command is generated so that the activation that results therefrom allows refreshing of the activation previously carried out for the pixel. To do this, a refresh time interval is determined, the duration of which defines the maximum space in time between two activations for a pixel. This interval of time may be common to all the pixels in the matrix or defined for each pixel or for various pixel subsets. It may for example be determined according to the retinal persistence of the human eye. This makes it possible to choose refresh interval values that are sufficiently great to prevent the display of redundant information at a high frequency to the detriment of the efficacy of the system, while taking account of the duration of the retinal persistence of the previous activation.

A second activation command signal can therefore be generated (403) in order to refresh the activation of the pixel during the interval of time thus determined and running as from the activation of the pixel following the previous activation command.

This previous activation command may be an activation command on event detection as described above, or a refresh activation command in the case for example where no activation command on event detection has been generated for a period corresponding to the refresh time interval running from the previous activation.

FIGS. 7a and 7b illustrate an asynchronous signal sequence for a pixel and the corresponding activation commands.

FIG. 7a illustrates the information carried by an asynchronous signal sample in which the events for a pixel are shown on a time axis by Dirac peaks of amplitude $G(t)$ corresponding to a level of grey. Five events $e_1$, $e_2$, $e_3$, $e_4$ and $e_5$ are shown on FIG. 7a, positioned respectively at instants $te_1$, $te_2$, $te_3$, $te_4$ and $te_5$ with respect to a time reference t0, with $te_1 < te_2 < te_3 < te_4 < te_5$. Each of the 5 events carries level of grey information for the relevant pixel denoted $g(t=te_i)$, with $i=\{1, 2, 3, 4, 5\}$.

These levels of grey values can for example result from the quantification of a level of grey value $2^{n_{quant}}$ levels and be coded in $n_{quant}$ bits.

FIG. 7b shows a simplified view of the sequence of events illustrated by FIG. 7a, where the events are represented by constant-amplitude Dirac peaks. The interval of time $\Delta t_p$ is defined according to the retinal persistence of the eye and so as to correspond to a maximum interval of time separating two consecutive activations of the same pixel. In the example illustrated in FIG. 7b, the differences in time separating two consecutive events do not exceed the quantity $\Delta t_p$, with exception of the separation between the events $e_2$ and $e_3$, $te_3 - te_2$.

In the example of a sequence of events illustrated in FIGS. 7a and 7b, it will be possible to generate a command activating the pixel following the detection of the event $e_1$ for an activation with the characteristics (typically a level of grey) carried by the asynchronous signal processed for the event $e_1$. The same applies to the events $e_2$, $e_3$, $e_4$ and $e_5$, the detections of which, in one embodiment, can each give rise to the generation of an activation command with respective characteristics.

In a particular embodiment of the proposed method, an activation command will also be generated in order to effect a refresh activation in a predetermined interval of time following the activation of the pixel on detection of the event $e_2$. This activation command may for example be generated if no event has been detected in the interval of time [$te_2$; $te_{2+}\Delta t_p$] of duration $\Delta t_p$ as from the instant $te_2$.

In a variant, it can be generated at any instant during the duration of the interval of time [$te_2$; $te_{2+}\Delta t_p$] of duration $\Delta t_p$ as from the instant $te_2$.

FIG. 7c shows an example of a sequence of activation commands generated according to one embodiment of the proposed method applied to the sequence of events in FIG. 7a. The activation commands are represented in the figure by variable-amplitude Dirac peaks. It shows activation commands $Ce_1$, $Ce_2$, $Ce_3$, $Ce_4$ and $Ce_5$, corresponding respectively to the events $e_1$, $e_2$, $e_3$, $e_4$ and $e_5$ in FIG. 7a, generated respectively at instants $tce_1$, $tce_2$, $tce_3$, $tce_4$ and $tce_5$. Each of the commands comprises an item of information relating to the level of grey at which the pixel must be illuminated denoted in the figure $g(te_i)$, with $i=\{1, 2, 3, 4, 5\}$.

Apart from the activation commands $Ce_i$ generated on detection of an event a refresh activation command $Cr,e_2$ is generated at the instant $t'e_2 + \Delta t_p$ following the non-detection of a new event following the detection of the event $e_2$ during a period $\Delta t_p$.

The refresh activation command $Cr,e_2$ can be generated with the same activation characteristics, and for example the same level of grey $g(te_2)$, as those included in the event-based activation command $Ce_2$. In a variant, the refresh activation command $Cr,e_2$ can be generated with activation characteristics determined according to those determined for the event-based activation command $Ce_2$.

The pixels of the matrix can also be refreshed in a group, and a systematic and periodic refreshing of pixels in the matrix can be carried out at a predetermined refresh frequency. The advantage of this embodiment is avoiding an individualised management of each pixel with regard to refreshing. The refreshing of the matrix is then repeated at a rate at least equal to the shortest refresh interval defined for a pixel.

According to this variant, the matrix of pixels is refreshed periodically, while remaining completely uncorrelated from and independent of the sequence of event-based activation commands. The generation of the activation refresh command is independent of the generation of the event-based activation command, and the activation refresh frequency is chosen so that the separation between an event-based activation of each pixel and the immediately subsequent refresh activation does not exceed a predetermined interval of time $\Delta t_p$ which, as discussed above, can be chosen according to the retinal persistence of the human eye of around 40 ms to 150 ms. This "mixed" activation mode makes it possible to combine an event-based activation functioning asynchronously with a periodic refresh activation carried out synchronously. Thus, according to the occurrence of events for each pixel, the refresh activation of the pixel can occur in a very short period of time following an event-based activation of the pixel, or at the end of a predetermined period following an event-based activation of the pixel defined as the maximum separation between two activations of the pixel. This mixed mode alleviates the management of the refreshing of the activation, while limiting, by means of the asynchronous event-based activation for each pixel, activation of the redundant information, since the asynchronous activation makes it possible to choose refresh frequencies that are short in comparison with current systems.

With reference to FIG. 1, each generation of an event-based activation command can for example give rise to the storage 103b by the data processing unit 102a of activation characteristics relating to the command generated, so that these characteristics can be recovered by the unit 102 for managing the refresh activation.

FIG. 7d shows schematically a series of activation commands generated according to another embodiment of the proposed method applied to the sequence of events in FIGS. 7a and 7b.

With reference to FIG. 7b, the event $e_4$ is detected with a time spacing $te_4 - te_3$ less than the interval of time $\Delta_{tmin}$ defined as the minimum interval of time separating two successive event-based activation commands of the pixel.

The sequence of activation commands in FIG. 7d differs from the sequence illustrated by FIG. 7c in that no activation command is generated for the event $e_4$, since the separation in time between the instant of detection of this event and the instant of detection of the immediately previous event is less than a predefined threshold $\Delta_{tmin}$.

Management of the separation time interval for each pixel can be done by means of a time delay, set to the value $\Delta_{tmin}$ defined for the pixel and triggered at each generation of an event-based activation command for the pixel. For example, an event detected while this time delay has not expired for the pixel can lead to ignoring the event and not generating a corresponding event-based activation command.

The activation characteristics carried by the asynchronous information for this ignored event can also be ignored. In a variant, it will be possible to provide an implementation according to which, even though no event-based activation command is generated, the activation characteristics corresponding to the event are stored 103b so as to be used subsequently, for example for the next refresh activation of the pixel.

According to the embodiment, a single time delay can be used for managing the refresh interval and managing the separation interval. This time delay can be triggered each time an activation command for the pixel is generated, storing an indicator for distinguishing the event-based activation commands from the refresh activation commands.

FIG. 8 shows a system for displaying a scene 800, comprising an acquisition sub-system 801 and a display sub-system 802.

The acquisition sub-system 801 comprises a light-acquisition device able to generate a signal carrying asynchronous information representing, for each pixel in a matrix of pixels, events corresponding respectively to variations in light in the scene. It is coupled operationally to the display sub-system 802, which comprises a display device as described above, comprising an input interface configured so as to receive a signal carrying asynchronous information.

The signal carrying asynchronous information passing over the coupling interface between the sub-systems 801 and 802 may have various forms, or formats, corresponding to various embodiments of the system. The coupling interface may moreover be designed in accordance with various standard formats, such as for example the USB format. The system proposed is not limited to a particular format of asynchronous information, or of the carrier of this information (for example, an asynchronous signal carrying information representing a flow of events), or a specific format of coupling interface between the sub-systems 801 and 802.

The asynchronous signal received by the sub-system 802 carries information representing temporal events corresponding to variations in light in a scene. To this end, the sub-system 802 may comprise an input interface configured so as to receive a signal produced by the acquisition sub-system 801.

FIG. 9a shows an example of implementation of the acquisition sub-system 801 according to a particular embodiment of the display system proposed.

FIG. 9a shows an acquisition sub-system 801 comprising a light-acquisition device 200 comprising an event-based asynchronous vision sensor (201) placed opposite a scene and receiving the light flow from the scene through an acquisition optic (202). The sensor (201) may comprise a group of photosensitive elements organised in a matrix of pixels, so that each pixel in the matrix corresponds to a photosensitive element of the sensor. For each pixel in the matrix, the device (200) generates an event-based asynchronous signal sequence from variations in light experienced by the pixel in the scene appearing in the field of vision of the device (200). Each pixel corresponding to a photosensitive element thus produces temporal events corresponding respectively to variations in light in the scene.

The sensor 201 therefore does not produce video frames formed by the matrix of pixels corresponding to the photosensitive elements of the sensor at a predetermined sampling frequency. It reacts for each pixel in the matrix to events corresponding to variations in light for the pixel. Conversely, it does not produce information for a pixel if no event occurs for this pixel. In particular it does not make any systematic capture of light intensity of the pixels of the matrix. Thus the events to which it reacts are asynchronous and do not depend on an acquisition frequency of video frames. This makes it possible to greatly reduce, if not eliminate, the redundancies created by the acquisition of video frames at a given rate not taking account of the absence of change in the information carried by a pixel from one frame to another.

A processing unit (203) processes the information issuing from the sensor (201) and representing events produced asynchronously by the various pixels, in order to generate an asynchronous signal carrying this information.

An example of a principle of acquisition by this asynchronous sensor is illustrated by FIGS. 9b-9d. According to this example, the information consists of a succession of instants, denoted $t_k$ (k=0, 1, 2, . . . ) at which an activation threshold Q is reached. The sensor 201 is therefore provided with a variation detector which, for each pixel, measures and records the light intensity of the pixel when this intensity has varied beyond a threshold Q.

FIG. 9b shows an example of a light-intensity profile P1 seen by a pixel in the matrix of the asynchronous vision sensor. Whenever this intensity increases by a quantity equal to the activation threshold Q in comparison with what it was at the instant $t_k$, a new event is identified and a positive line (level +1 in FIG. 9c) is emitted, corresponding to the instant at which the differential threshold Q, denoted $t_{k+1}$, was exceeded. Symmetrically, whenever the intensity of the pixel decreases by the quantity Q in comparison with what it was at the instant $t_{k'}$, a new event is identified and a negative line (level −1 in FIG. 9c) is emitted, corresponding to the instant at which the differential threshold Q, denoted $t_{k'+1}$, was exceeded.

FIG. 9d shows the intensity profile P2 that can be reconstructed as an approximation of the profile P1 by integration in time of the asynchronous signal in FIG. 9c.

The activation threshold Q can be fixed, as in the case of FIGS. 9b-d, or adaptive according to the light intensity. For example, the threshold ±Q can be compared with the variations in the logarithm of the light intensity for the generation of an event ±1.

The class of asynchronous photosensitive sensors generating events from variations in light intensity is designated by the acronym DVS, standing for dynamic vision sensor.

By way of example, the sensor 201 may be a DVS sensor of the type described in "A 128×128 120 dB 15 µs Latency Asynchronous Temporal Contrast Vision Sensor", P. Lichtsteiner, et al., IEEE Journal of Solid-State Circuits, Vol. 43, No. 2, February 2008, pages 566-576, or in the patent application US 2008/0135731 A1.

Another generation of asynchronous photosensitive sensors makes it possible to generate asynchronous information indicating events as well as an associated characteristic, for example a level of grey.

The article by Posch, C., Matolin, D., and Wohlgenannt, R. (2011) entitled "A qvga 143 db dynamic range frame-free pwm image sensor with lossless pixel-level video compression and time-domain cds", and published in the IEEE Journal of Solid-State Circuits, 46, pages 259-275. doi: 10.1109/JSSC.2010.2085952, provides a description of examples of events coded by levels of grey.

The asynchronous information for each pixel there also consists of a succession of pulses or lines positioned in time at the instants $t_k$ dependent on the light profile for the pixel. Each event may for example correspond to successive pulses, the first indicating the instant of the event and the second making it possible to determine a level of grey for the pixel according to the difference in time between the two pulses. The information corresponding to an event for a pixel thus comprises a first item of information relating to an instant of occurrence of the event, and a second item of information relating to a light characteristic (level of grey) for the pixel at this instant.

The acquisition sub-system 801 may incorporate, in one embodiment, a new-generation event-based asynchronous vision sensor 201, which is sometimes referred to by the acronym ATIS, standing for "Asynchronous Time-based Image Sensor". The acquisition sub-system and the ATIS sensor that it incorporates may for example be of the type described in the article by C. Posch et al., entitled "An Asynchronous Time-based Image Sensor" (IEEE International Symposium on Circuits and Systems, 2008, pages 2130-2133), or of the type described in the article by C. Posch et al., entitled "A QVGA 143 dB dynamic range frame-free PWM image sensor with lossless pixel-level video compression and time-domain CDS" (46(1): 259275, 2011).

The dynamic range of the retina (the minimum period between the action potentials) of around a few milliseconds can suitably be reproduced with a sensor of the DVS or ATIS type. The dynamic performance is in any event greatly superior to what can be expected with a conventional video camera with a realistic sampling frequency. For example, a sensor of this type makes it possible to achieve temporal resolutions of around one microsecond with a luminance range greater than 120 dB, which is very much superior to a standard CMOS/CCD camera, which typically has a luminance range of 60-70 dB.

In one embodiment, the processing unit 203 comprises a processor coupled operationally to a memory. The memory may contain software instructions which, when they are executed by the processor of the data-processing unit, cause this unit to process the signals received from the sensor and generate the asynchronous information representing, for each pixel, events corresponding to variations in light concerning the pixel according to the various methods described herein, and transmission of the asynchronous information over an output interface. The processing unit may be a component implementing a processor or a computing unit for generating asynchronous information according to the various methods described and controlling the asynchronous vision sensor of the device 200 in the sub-system 801.

Furthermore, the processing unit, and in particular its processor and/or its memory means, may, separately or conjointly, be implemented in software form, as described above, in hardware form, such as an application-specific integrated circuit (ASIC), or in the form of a combination of hardware and software elements, such as for example one or more software programs intended to be loaded and executed respectively on one or more components of the FPGA (field programmable gate array) type. They may be implemented, separately or conjointly, in the form of an electronic circuit, or in one or more electronic components (chip or chipset).

Figure 5D:
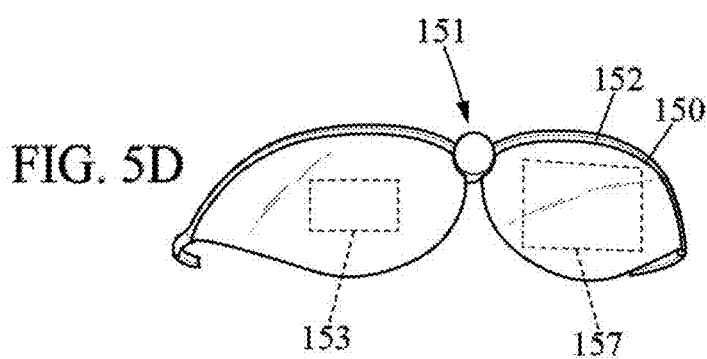

With reference to FIGS. 5b, 5c and 5d, the asynchronous vision sensor may be mounted on the support on which the projector is mounted. FIGS. 5b, 5c and 5d show the example embodiment in which the support is a pair of spectacles 150. The sensor 151 is mounted on the top part 152 of the spectacles frame. Preferably, the sensor will be mounted centred on the top part 152 of the spectacles, so as to avoid parallax errors between the acquired scene and the one reproduced by stimulation of photoreceptors of an eye by the projector 153.

In a variant, provision can be made for disposing the sensor on a surface of the spectacles, such as the surface—internal or external—of one of the lenses of the spectacles 150.

"Lens of a spectacle" or "spectacle lens" means a part of the spectacles with a surface form fixed under the top part of the spectacles, and which may consist of glass but also any other material, not necessarily translucent. A pair of spectacles comprises two spectacle lenses, each spectacle lens being formed by an internal surface and an external surface.

When the projector 153 is mounted on a first surface 158 of the spectacles 150, the control unit of the device and the processing unit of the acquisition sub-system may be mounted on a second surface 159 of the spectacles. These two units may be implemented on an electronic module 157 fixed to the internal surface of a lens of the spectacles, and the projector 153 being fixed to the internal surface of the other spectacle lens, as illustrated in FIGS. 5b and 5d.

In a variant, an optoelectronic unit consisting of the sensor, the control unit of the device and the processing unit of the acquisition sub-system may be mounted on a surface of one of the lenses of the spectacles, the projector being mounted on a surface of the other spectacle lens or on the other surface of the same spectacle lens.

Although described through a certain number of detailed example embodiments, the activation control method and equipment for implementing the method comprise different variants, modifications and improvements that will be obvious to a person skilled in the art, it being understood that these different variants, modifications and improvements form part of the scope of the invention, as defined by the following claims.

In addition, various aspects and features described above may be implemented together, or separately, or be substituted for one another, and all the various combinations and sub-combinations of the aspects and features form part of the scope of the invention. Furthermore, it may be that some systems and items of equipment described above do not incorporate all the modules and functions described for the preferred embodiments.

The information and signals described in the present document may be represented in accordance with a multitude of technologies and techniques. For example, the instructions, messages, data, commands, information, signals, bits and signals may be represented by voltages, currents, electromagnetic waves or a combination thereof.

According to the embodiment chosen, some deeds, actions, events or functions of each of the methods described in the present document may be performed or occur in an order different from that in which they have been described, or may be added, merged or not be performed or not occur, according to the circumstances. Furthermore, in some embodiments, some deeds, actions or events are performed or occur concurrently rather than successively.

The invention claimed is:

1. Device for displaying a sequence of images in the form of a matrix of pixels, comprising a control unit coupled operationally to a projector, the control unit comprising
an input interface configured so as to receive asynchronous information representing, for each pixel in the matrix, events concerning the pixel; and
a processor configured so as to demand the activation of each pixel in the matrix at instants determined by respective events indicated by the asynchronous information for said pixel;
in which the projector is arranged on a support so as to illuminate photoreceptors of the eye during the use of a device, and configured to project a light stream relative to the pixels activated by the control unit,
wherein the control unit is further configured so as, after activation of a pixel in the matrix at an instant determined by an event indicated by the asynchronous information, to repeat the command for activation of said pixel substantially at the same activation level at instants defined by a refresh sequence.

2. The device according to claim 1, in which the projector comprises a matrix of micromirrors, a unit controlling the matrix of micromirrors, a control input for receiving the pixel-activation commands, and an optical input for receiving a light stream.

3. The device according to claim 1, in which the projector support is in the form of a pair of spectacles, the projector being placed on a surface of the spectacles.

4. System for displaying a scene, comprising a display sub-system coupled operationally to an acquisition sub-system, in which:
   the display sub-system comprises a device according to claim 1;
   the acquisition sub-system comprises a sensor disposed opposite the scene, coupled operationally to a processing unit configured so as to generate asynchronous information representing events for each pixel.

5. The system according to claim 4, in which the sensor is a light sensor comprising a optic for acquiring the scene and a matrix of photosensitive elements.

6. The system according to claim 4, in which the sensor is mounted on the projector support so that the captured scene corresponds substantially to the visual field of a user of the device.

7. The system according to claim 4, in which:
   the projector support is in the form of a pair of spectacles,
   the projector is mounted on a first surface of the spectacles;
   the sensor is mounted on a top part of the spectacles frame;
   the control unit of the device and the processing unit of the acquisition sub-system are mounted on a second surface of the spectacles.

8. The system according to claim 4, in which:
   the projector support is in the form of a pair of spectacles,
   the projector is mounted on a first surface of the spectacles;
   the sensor, the control unit of the device and the processing unit of the acquisition sub-system are mounted on a second surface of the spectacles.

* * * * *